(12) United States Patent
Peyman

(10) Patent No.: US 6,918,904 B1
(45) Date of Patent: Jul. 19, 2005

(54) METHOD OF RESHAPING THE CORNEA BY CONTROLLED THERMAL DELIVERY

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 35 days.

(21) Appl. No.: 09/986,141

(22) Filed: Nov. 7, 2001

(51) Int. Cl.⁷ ............................................. A61F 9/007
(52) U.S. Cl. .............................. 606/5; 606/10; 606/13; 607/104
(58) Field of Search .... 606/3–5, 10–14; 607/100–104; 604/20

(56) References Cited

U.S. PATENT DOCUMENTS

| | | | |
|---|---|---|---|
| 3,776,230 A | 12/1973 | Neefe | |
| 3,831,604 A * | 8/1974 | Neefe | 604/20 |
| 4,523,594 A * | 6/1985 | Kuznetz | 607/104 |
| 4,718,418 A | 1/1988 | L'Esperance, Jr. | |
| 4,807,623 A | 2/1989 | Lieberman | |
| 4,840,175 A | 6/1989 | Peyman | |
| 4,903,695 A * | 2/1990 | Warner et al. | 606/5 |
| 4,976,709 A * | 12/1990 | Sand | 606/5 |
| 4,994,058 A | 2/1991 | Raven et al. | |
| 5,104,957 A * | 4/1992 | Kelman et al. | 527/201 |
| 5,196,027 A | 3/1993 | Thompson et al. | |
| 5,215,104 A | 6/1993 | Steinert | |
| 5,336,261 A | 8/1994 | Barrett et al. | |
| 5,591,185 A | 1/1997 | Kilmer et al. | |
| 5,722,971 A | 3/1998 | Peyman | |
| 5,779,696 A * | 7/1998 | Berry et al. | 606/5 |
| 5,833,701 A | 11/1998 | Gordon | |
| 5,919,185 A | 7/1999 | Peyman | |
| 5,935,140 A | 8/1999 | Buratto | |
| 5,964,748 A | 10/1999 | Peyman | |
| 6,024,095 A | 2/2000 | Stanley, III | |
| 6,086,204 A | 7/2000 | Magnante | |

* cited by examiner

*Primary Examiner*—David M. Shay
(74) *Attorney, Agent, or Firm*—Bell Boyd & Lloyd PLLC; Jeffrey J. Howell

(57) ABSTRACT

A method of correcting the refractive error in the cornea of an eye. The cornea is heated, to loosen the molecules therein, thereby softening the cornea into a gelatinous material. The gelatinous material is then reshaped, so that it substantially conforms to a predetermined pattern, and cooled to maintain it in the predetermined pattern. This results in modification of the cornea without a gray to white response in the cornea and corneal tissue shrinkage.

14 Claims, 5 Drawing Sheets

METHOD OF RESHAPING THE CORNEA BY CONTROLLED THERMAL DELIVERY

RELATED APPLICATIONS

Related subject matter is disclosed in U.S. patent application Ser. No. 09/532,516, filed Mar. 21, 2000; entitled "An Adjustable Universal Implant Blank for Modifying Corneal Curvature and Methods of Modifying Corneal Curvature Therewith", the entire contents of which are incorporated herein by reference.

FIELD OF THE INVENTION

The present invention relates to a method for correcting the refractive error in the cornea of an eye. In particular, the cornea is modified by positioning a reshaping device having a predetermined first surface adjacent a surface of the cornea. The reshaping device is then heated, which in turn heats the surface of the cornea and softens the portion of the cornea underlying the reshaping device, so that the softened corneal surface substantially conforms to the predetermined first surface of the reshaping device.

DESCRIPTION OF RELATED PRIOR ART

A normal emetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused behind the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of eyeglasses or contact lenses, to correct vision disorders. A common method of correcting myopia is to place a "minus" or concave lens in front of the eye to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia, or in eyes suffering from hypermetropic, hyperopic or astigmatic conditions which are not very severe, these methods are ineffective in correcting vision in eyes suffering from severe forms of ametropia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then thawed and reattached to the main portion of the live cornea. Hence, it is intended that the reshaped cornea will change the position at which the light entering the eye through the cut portion is focused, so that hopefully the light is focused directly on the retina, thus remedying the ametropic condition.

The myopic keratomileusis technique is known to be effective in curing myopic conditions within a high range. However, the technique is impractical because it employs very complicated and time consuming freezing, cutting and thawing processes.

Keratophakia is another known surgical technique for correcting severe ametropic conditions of the eye by altering the shape of the eye's cornea. In this technique an artificial, organic or synthetic lens is implanted inside the cornea to thereby alter the shape of the cornea and thus change its refractive power. Accordingly, as with the myopic keratomileusis technique, it is desirable that the shape of the cornea be altered to a degree that allows light entering the eye to be focused correctly on the retina.

However, the keratophakia technique is relatively impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M.D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomileusis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outwardbulging (eklasia), this technique is not especially effective in correcting very high myopia. That is, a typical live cornea is on average about 500 microns thick.

The laser ablation technique requires that at least about 200 microns of the corneal stroma remain after the ablation is completed so that instability and outwardbulging does not occur. Hence, this method typically cannot be effectively used to correct high myopia of greater than 15 diopters because, in order to reshape the cornea to the degree necessary to alter its refractive power to sufficiently correct the focusing of the eye, too much of the cornea would need to be ablated.

Additionally, the cornea can be modified using thermal coagulation. In thermal coagulation, electrodes of varying shapes are applied to the cornea in a predetermined pattern. The electrodes emit a radio frequency wave or laser light, thereby heating the surface of the cornea. Once the surface of the cornea is heated it tends to shrink, the shrinking of the cornea changes the refractive properties of the eye. In these methods, the thermal temperature generally rises in the surface of the cornea and in the deeper tissue above the coagulation threshold, producing clinical appearance of a gray to white response in the cornea, or protein detanurization. Furthermore, since the cornea can generally only be shrunk in response to thermal coagulation, this method is exclusively used for presbyopic and hyperopic correction of refractive errors.

Therefore, it is apparent that a need therefore exists for improved methods for further modifying the cornea to better correct ametropic conditions.

SUMMARY OF THE INVENTION

Accordingly, it is an object of the present invention to provide a method for adjusting the shape of a live cornea to correct high ametropic conditions.

Another object of the invention is to provide a method for modifying the shape of a live cornea to correct ametropic conditions without laser ablation.

Another object of the present invention is to provide a method for adjusting the shape of a live cornea by heating the cornea so that it softens and reforms to the shape of an lens positioned adjacent the cornea.

A further object of the present invention is to provide a method for modifying the cornea of an eye that allows for corrective measures that avoid or eliminate outwardbulging or instability in the cornea.

Still another object of the present invention is to provide a method for modifying the cornea of an eye without a gray to white response and tissue shrinkage.

Yet another object of the present invention is to provide a method for modifying the cornea of an eye that can be used for at least presbyopic, hyperopic and myopic correction of refractive errors.

The foregoing objects are basically attained by a method of correcting the refractive error in the cornea of an eye, comprising the steps of heating the cornea to loosen the molecules therein, thereby softening the cornea into a gelatinous material, reshaping the gelatinous material, so that it substantially conforms to a predetermined pattern, and cooling the reshaped gelatinous material to maintain it in the predetermined pattern.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE PREFERRED EMBODIMENT

Figure 1:
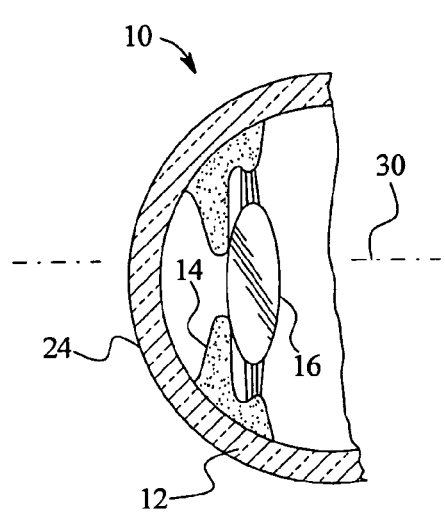
FIG. 1 is a side elevational view in cross section taken through the center of an eye showing the cornea, pupil and lens.

FIG. 1 is a side elevational view in cross section taken through the center of an eye 10, which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

As seen in FIGS. 1–7, the refractive properties of the eye can be modified or altered by forming a flap 18 in the surface 12 of the cornea, preferably by placing a reshaping device 20 having a predetermined shape on the surface 12 of the cornea, heating the reshaping device and in turn heating the surface of the cornea. However, it is noted that the cornea can be heated by any means suitable, such as directly by a laser or chemically or any other method that would allow heating the cornea to the proper temperature. Heating the cornea to the predetermined temperature causes the corneal stroma to soften and have a gel-like or gelatinous consistency. The gelatinous corneal portion then can flow and reform to take the form of the interior surface 32 of the reshaping device, thus changing the refractive properties of the cornea and the eye.

To begin, the refractive error in the eye is measured using wavefront technology, as is known to one of ordinary skill in the art. A more complete description of wavefront technology is disclosed in U.S. Pat. No. 6,086,204 to Magnate, the entire content of which is incorporated herein by reference. The refractive error measurements are used to determine the appropriate shape of lens or contact 20 to best correct the error in the patient's cornea. Preferably, the lens 20 is manufactured or shaped prior to the use of the wavefront technology and is stored in a sterilized manner until that specific lens shape or size is needed. However, the information received during the measurements from the wavefront technology can be used to form the lens using a cryolathe, or any other desired system or machine.

Figure 2:
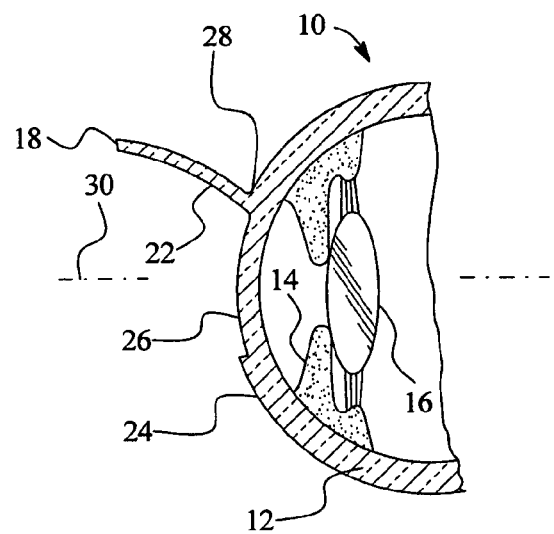
FIG. 2 is a side elevational view in cross section of the eye of FIG. 1 with a flap formed in the surface of the cornea.
Figure 3:
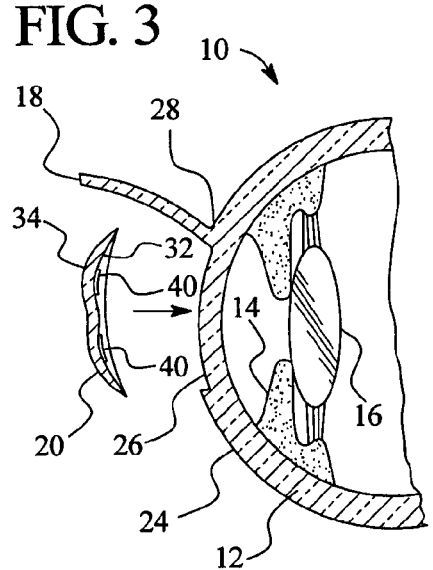
FIG. 3 is a side elevational view in cross section of the eye of FIG. 2 with a reshaping device having a predetermined shape for correcting myopia proximate to the exposed surface of the cornea.

Preferably, a flap or portion 18 can be formed in the surface 24 of the cornea 12, as seen in FIG. 2. Preferably the flap is formed in the stromal layer of the cornea, but does not necessarily need to be formed in the stromal layer and can be formed in any desired portion of the cornea. The flap may be formed be any means desired, such as with a knife, microkeratome, or with a laser. Preferably an internal area of the cornea is separated into first and second substantially circular shaped internal surfaces 22 and 26, respectively, to form the circular shaped corneal flap 18. First internal surface 22 faces in a posterior direction of cornea 12 and the second internal surface 26 faces in anterior direction of the cornea 12. The flap 18 preferably has a uniform thickness of about 10–250 microns, and more preferably about 80–100 microns, but can be any suitable thickness. A portion 28 of flap 18 preferably remains attached to the cornea by an area at the periphery of the flap. However, the flap can be any suitable configuration, such as a flap attached to the cornea at a location other than at the periphery or a flap that is not attached to the cornea at all. Additionally, the flap may be shaped or sized as desired and does not need to be circular.

The flap is moved or pivoted about portion 28 using any device known in the art, such as a spatula or microforceps or any other device, to expose the first and second corneal surfaces 22 and 26, respectively. The flap preferably exposes a portion of the corneal surface that intersects the main optical axis 30 and allows uninhibited access thereto.

Figure 4:
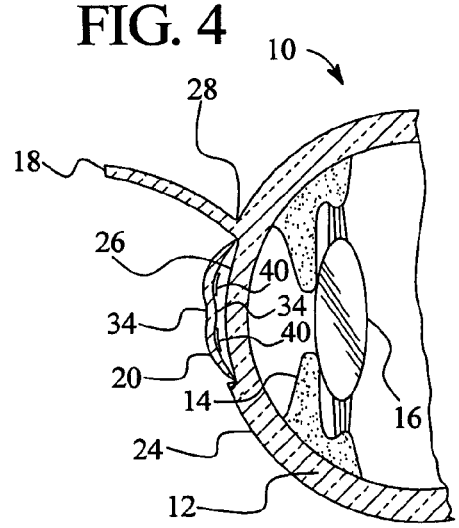
FIG. 4 is a side elevational view in cross section of the eye of FIG. 3 with the reshaping device immediately adjacent and overlying the exposed surface of the cornea.

Lens or shield 20 can then be positioned adjacent and overlying the surface 22 of the cornea, as seen in FIG. 4. However, it is noted that the lens does not necessarily need to be positioned adjacent a surface exposed by a flap and may be positioned on the external surface 24 of the cornea 12 or the second internal surface 26. The surface exposed by the flap is the preferred method, since the cornea will not develop tissue necrosis, which may be possible, if the lens is positioned adjacent the external surface of the cornea.

Lens 20 is preferably any metal that can absorb heat and transmit and distribute heat throughout the lens in a uniform or substantially uniform manner. However, the lens does not necessarily need to be metal and can be any synthetic or semi-synthetic material, such as plastic or any polymer or any material that has pigmentation that would allow the lens to absorb the heat from the laser and transmit and distribute the heat uniformly throughout the lens.

Additionally, lens 20 is substantially circular and has a first or inner side or surface 32 and a second or outer side or surface 34 and preferably has a substantially concave shape. The lens preferably has a predetermined shaped, or more specifically, the first surface 32 preferably has a predetermined shape that would be the proper shape of the surface 26 of the cornea plus the flap 18 to focus light onto the retina. In other words, if the interior of the cornea were the shape of the interior surface of the lens the patient would be able to have 20/20 vision or better.

FIGS. 1–7 show the correction of myopic error using a concave lens 20. However, the lens can be formed such as lens 120, shown in FIGS. 8–12 and discussed below, for correction of hyperopic error or any other shape desired for the correction of astigmatic error or any other error.

Figure 5:
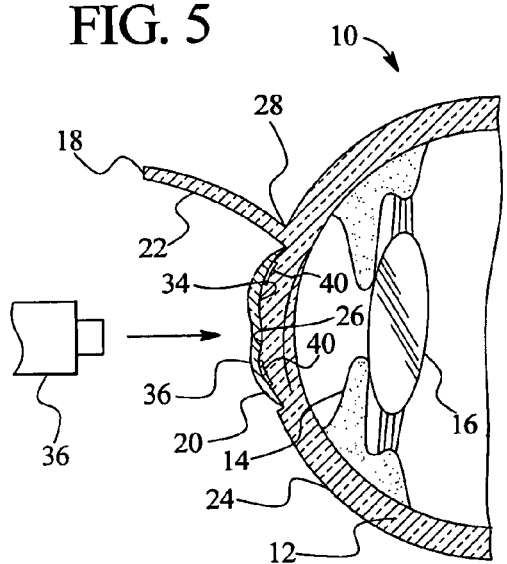
FIG. 5 is a side elevational view in cross section of the eye of FIG. 4 with a laser irradiating the reshaping device to soften the cornea with the softened portion of the cornea conforming to the internal shape of the reshaping device.

Once the reshaping device is positioned immediately adjacent the exposed surface 26 of the cornea 12, a heating device is applied or administered to the reshaping device 20, which in turn transfers the heat to the surface of the cornea. Preferably as seen in FIG. 5, a laser 36 is aimed and fired or directed, so that the light emitted form the laser or the laser beam L is absorbed by the reshaping device 20 and then absorbed by or transferred to the cornea. Preferably, the laser beam is in the infrared portion of the electromagnetic spectrum, such as light supplied by a Nd-Yag laser at 1.32 $\mu$m, a Holmium laser at 2.2 $\mu$m or a Erb-Yag laser at 2.9 $\mu$m, or any other laser light wave length that is absorbed by water. For example, the laser light can be from a $CO_2$ laser or a visible light laser, such as an argon laser. Additionally, the reshaping device can be heated by any means suitable, such as microwaves.

The laser beam preferably heats the lens so that the inner surface of the reshaping device is about or below 60° Celsius (140° F.), which in turn heats the corneal surface 26 (preferably the stroma) to about the same temperature, thereby softening the cornea. The reshaping device inner surface temperature is constantly controlled or measured, preferably using multiple thermal couples 40 on the inner surface of the reshaping device. The thermal couples are linked to a computer control system (not shown) using any method known in the art, such as direct electrical connection or wires or a wireless system. The computer control system monitors the temperature and controls the laser to change the temperature of the reshaping device. The computer can maintain a precise constant temperature, increase temperature or decrease temperature as desired, and at any rate desired. This computer control system, along with the thermal couples ensure an adequate and precise temperature, since heating the cornea above 60° Celsius can cause coagulation of the cornea.

Figure 6:
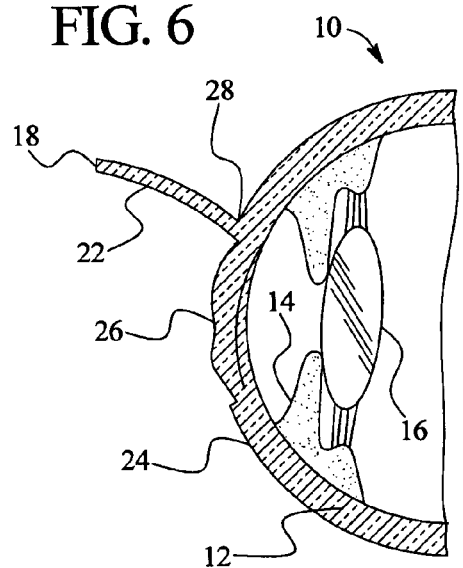
FIG. 6 is a side elevational view in cross section of the eye of FIG. 5 with the reshaping device removed and the cornea maintaining its reformed shape.

By heating the corneal stroma to about or below 60° C., the molecules of the cornea are loosened, and the cornea changes from a substantially solid substance to a gelatinous substance or gel-like substance. However, the corneal temperature is maintained at or below 60° C., and therefore, protein denaturization does not occur as with conventional thermal coagulation. Since the heated portion of the cornea is now flowable, the cornea reforms and is molded to take the shape of the inner surface 32 of the reshaping device, thereby forming the cornea into the reformed, corrected shape in an effort to provide the patient with 20/20 vision. The cornea is then cooled by applying cool or cold water, by applying air or by simply removing the heated reshaping device or the heat from the reshaping device and using the ambient air temperature. As the cornea cools, it is held by the reshaping device 20 to the preferred shape, which becomes its new permanent shape once the cornea is completely cooled and changes from its gel-like consistency to its original substantially solid consistency, as shown in FIG. 6.

Figure 7:
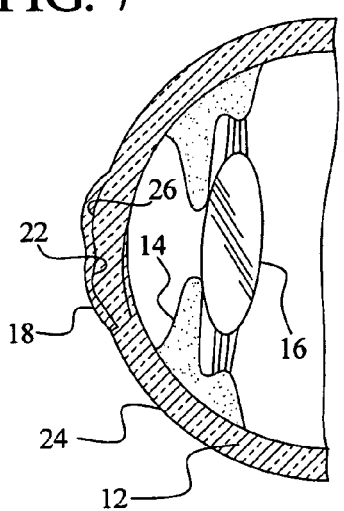
FIG. 7 is a side elevational view in cross section of the eye of FIG. 6 with the flap repositioned over the reformed exposed surface of the cornea.
Figure 8:
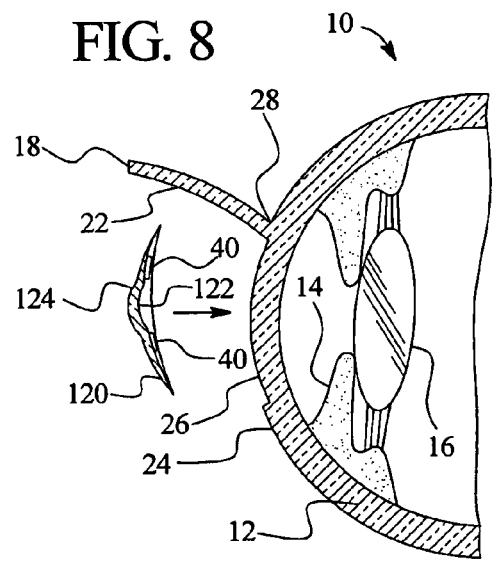
FIG. 8 is a side elevational view in cross section of the eye of FIG. 2 with a reshaping device having a predetermined shape for correcting hyperopia proximate to the exposed surface of the cornea.
Figure 9:
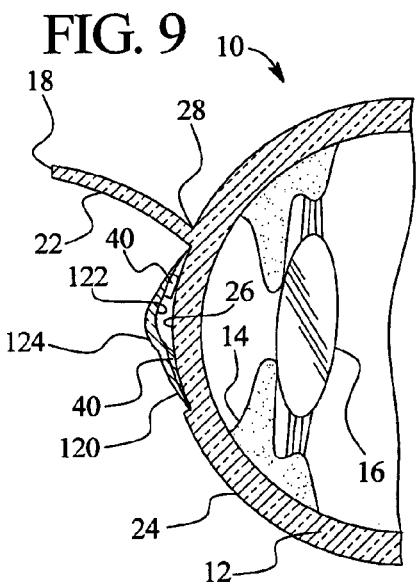
FIG. 9 is a side elevational view in cross section of the eye of FIG. 8 with the reshaping device immediately adjacent and overlying the exposed surface of the cornea.
Figure 10:
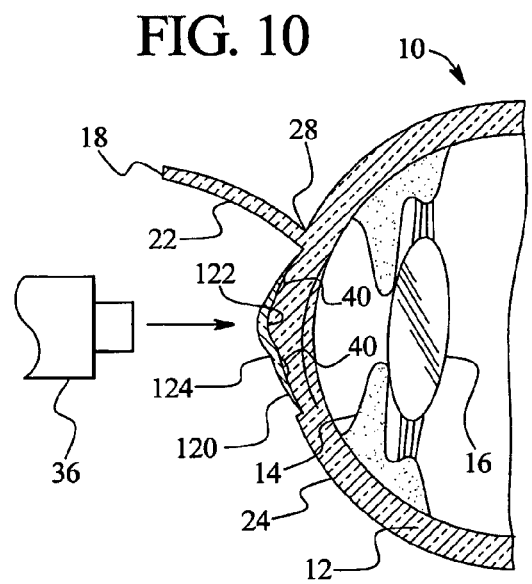
FIG. 10 is a side elevational view in cross section of the eye of FIG. 9 with a laser irradiating the surface of the cornea to soften the cornea with the softened portion of the cornea conforming to the internal shape of the reshaping device.
Figure 11:
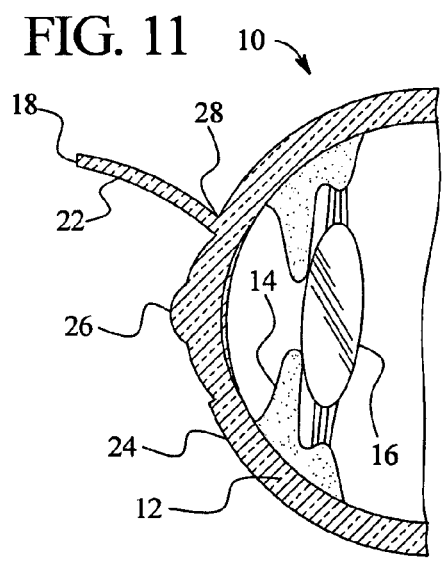
FIG. 11 is a side elevational view in cross section of the eye of FIG. 10 with the reshaping device removed and the cornea maintaining its reformed shape.
Figure 12:
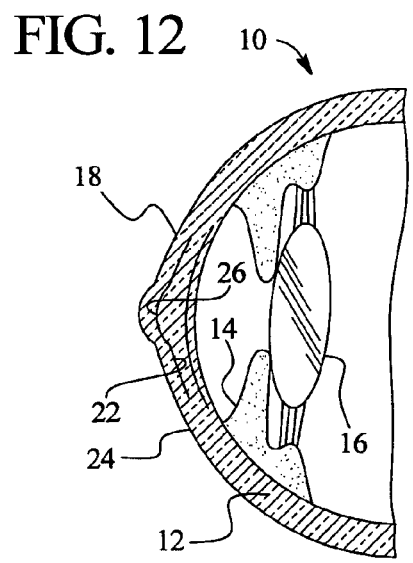
FIG. 12 is a side elevational view in cross section of the eye of FIG. 11 with the flap repositioned over the reformed exposed surface of the cornea.

The flap 18 is then replaced so that it covers or lies over the first surface 26 of the cornea 12 in a relaxed state, as seen in FIG. 7. This new permanent shape allows the cornea to properly focus light entering the eye on the retina. The refractive power of the eye is then measured to determine the extent of the correction. If necessary the method can be repeated.

A reshaping lens can be applied to the external surface of the cornea, if necessary, after the flap has been replaced to maintain the proper corneal curvature or the eye can be left to heal with no additional reshaping lens being used.

Furthermore, at the end of the method, if desired, topical agents, such as an anti-inflammatory, antibiotics and/or an antiprolifrative agent, such as mitomycin or thiotepa, at very low concentrations can be used over the ablated area to prevent subsequent haze formation. The mitomycin concentration is preferably about 0.005–0.05% and more preferably about 0.02%. A short-term bandage contact lens may also be used to protect the cornea.

By reforming the cornea into the desired shape in this manner, a highly effective surgical method is formed that allows perfect or near perfect vision correction without the need to ablate any of the cornea or causing a gray to white response in the cornea of the eye.

FIGS. 8–12

As shown in FIGS. 8–12, the same general method as shown in FIGS. 1–7 can be used to correct hyperopic error in the cornea. In this method, a substantially circular convex reshaping device 120, rather than concave reshaping device 20, having a first or inner surface 122 and a second or outer surface 124, is used and placed immediately adjacent and overlying the surface 26 of the cornea. A heating element, preferably a laser 36, is used to heat the reshaping device, which in turn increases the temperature of the cornea to about or below 60° Celsius, as described above. This heating causes the cornea to soften and turn into a gel-like material, thereby becoming flowable to conform to the inner surface 122. Once the corneal surface 26 is cooled and permanently reformed to the inner surface of the reshaping device, the device is removed and the flap replaced. The hyperopic error is corrected and the cornea can now effectively focus light on the retina, as described above.

This method for correcting hyperopic conditions is substantially similar to the method for correcting myopic conditions. Thus, the entire method described above for correcting myopic error of the cornea applies to the correction of hyperopic error, except for the exact configuration of the reshaping device.

Figure 13:
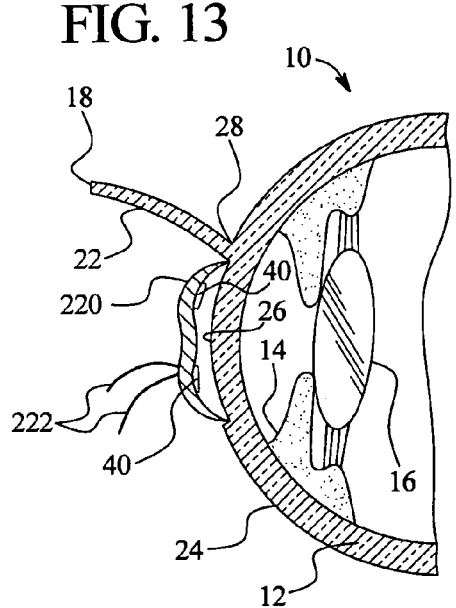
FIG. 13 is a side elevational view in cross section of the eye of FIG. 2 with a thermally conductive reshaping device having a predetermined shape immediately adjacent the exposed surface of the cornea.
Figure 14:
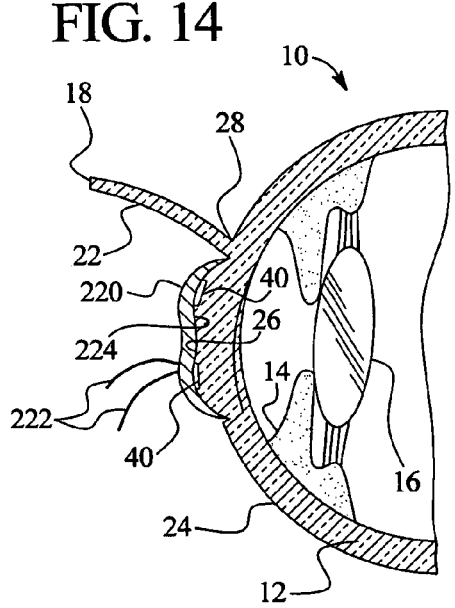
FIG. 14 is a side elevational view in cross section of the eye of FIG. 13 with the thermally conductive reshaping device administering controlled heat to the exposed surface of the cornea to soften the cornea with the softened portion of the cornea conforming to the internal shape of the reshaping device.

FIGS. 13 and 14

As shown in FIGS. 13 and 14, the reshaping device can be a thermally conductive plate or reshaping device 220 that is electrically connected to a power source (not shown) using electrical wires 222. The thermally conductive plate 220 is preferably any metal or conductive material that can conduct electricity supplied by a power source (not shown) and turn the electricity into heat. Furthermore, the plate preferably is formed from a material that would allow an equal or substantially uniform distribution of heat through the plate.

This method is similar to those described above; however, the temperature of the cornea is increased using the thermocouple plate instead of a laser. As seen in FIG. 13, the plate 220 is heated to the desired temperature, preferably about or below 60° Celsius, as described above. This causes loosening of the corneal molecules or softening of the cornea, which allows the cornea to conform to surface 224 of plate 220, thereby permanently changing the shape of the cornea. Once the corneal surface 26 has cooled and permanently reformed to the inner surface of the thermocouple plate, the plate is removed and the flap replaced. The cornea can now effectively focus light on the retina, as described above.

Although, the method is shown in FIGS. 13 and 14 using a thermally conductive plate to correct myopic error, a thermally conductive plate can be used to change the shape of the cornea in any manner desired, such to correct astigmatic or hyperopic error in the cornea.

Furthermore, since this method is substantially similar to the methods described above, the description of those methods and references numerals used therein, excluding the specific lens and heating element, apply to this method.

Figure 15:
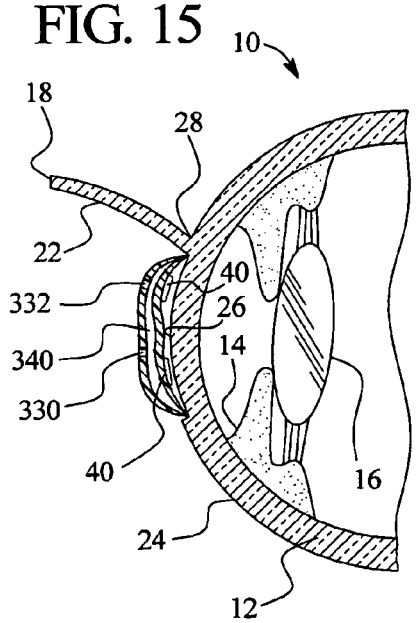
FIG. 15 is a side elevational view in cross section of the eye of FIG. 2 with a reshaping device having two passageways for irrigation and aspiration of a liquid with a predetermined temperature and having a predetermined shape immediately adjacent the exposed surface of the cornea.
Figure 16:
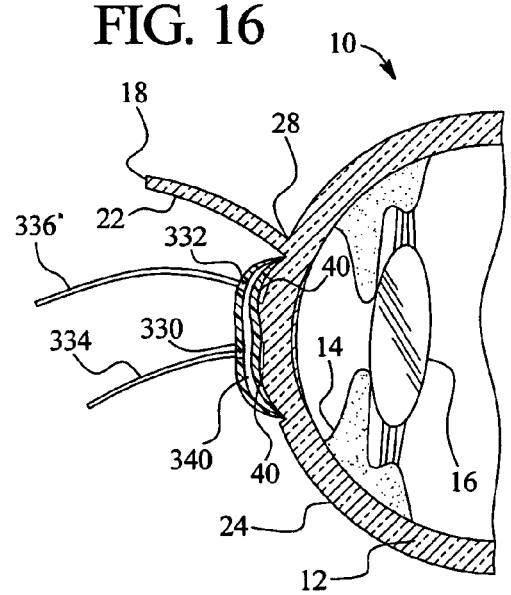
FIG. 16 is a side elevational view in cross section of the eye of FIG. 15 with the aspiration and irrigation tubes extending through the reshaping device for administering and removing liquid with a predetermined temperature to the exposed surface of the cornea to soften the cornea with the softened portion of the cornea conforming to the internal shape of the reshaping device.
Figure 17:
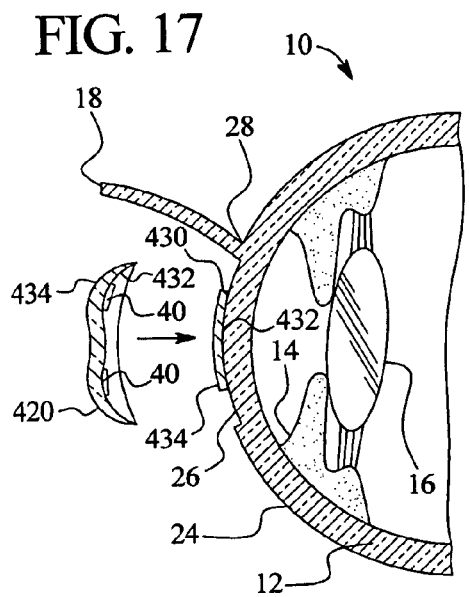
FIG. 17 is a side elevational view in cross section of the eye of FIG. 2 with a inlay positioned on the exposed surface of the cornea and with a reshaping device having a predetermined shape for correcting myopia proximate to the inlay.
Figure 18:
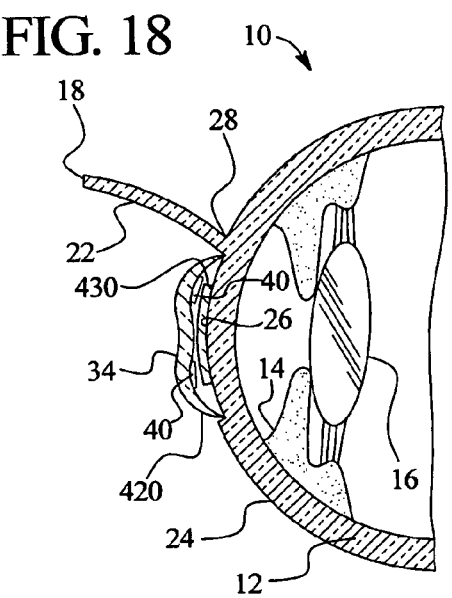
FIG. 18 is a side elevational view in cross section of the eye of FIG. 17 with the reshaping device immediately adjacent the inlay.
Figure 19:
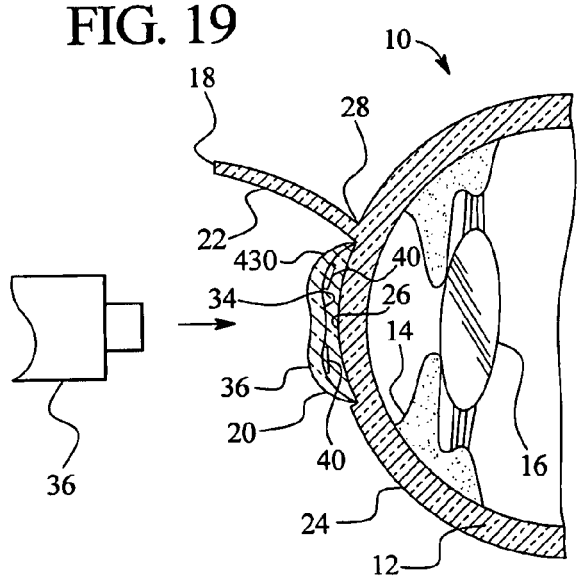
FIG. 19 is a side elevational view in cross section of the eye of FIG. 18 with a laser irradiating the lens to soften the inlay with the softened portion of the inlay conforming to the internal shape of the lens.

FIGS. 15 and 16

As shown in FIGS. 15 and 16, reshaping device 320 can be a container, i.e., hollow, with an irrigation port 330 and an aspiration port 332 providing access to interior chamber 340. Reshaping device 320 is preferably any metal or plastic that can be filled with a liquid and absorb heat and distribute the heat throughout the reshaping device in a uniform or substantially uniform manner. However, the reshaping device does not necessarily need to be metal and can be any synthetic or semi-synthetic material, such as plastic or any polymer of any material that would allow the lens to absorb the heat from the liquid and distribute the heat uniformly throughout the reshaping device.

The method of FIGS. 15–16 is similar to those described above; however, the temperature of the cornea is increased using a tube 334 that couples to the irrigation port and fills chamber 340 of the container with a liquid of a predetermined temperature, preferably about or below 60° Celsius (140° F.). Once filled with the liquid, the inner surface of the reshaping device would increase to the desired temperature, thereby loosening the molecules of the cornea or softening surface 26 of the cornea, which allows the cornea to conform to surface 324 of reshaping device 320 and results in the proper reformation of the cornea. The liquid can then be removed from the container via the aspiration tube 236, allowing the cornea to cool and permanently reform to the desired shape, as described above. Once the corneal surface 26 has cooled and permanently reformed to the inner surface of the reshaping device, the reshaping device is removed and the flap replaced. The cornea can now effectively focus light on the retina, as described above.

Although, the method shown in FIGS. 15 and 16 uses a container to correct myopic error, this method can be used to change the shape of the cornea in any manner desired, such to correct astigmatic or hyperopic error in the cornea.

Furthermore, since this method is substantially similar to the methods described above, the description of those methods along with the reference numerals used therein, excluding the specific reshaping device and heating element, apply to this method.

FIGS. 17–20

As seen in FIGS. 17–20, a modified method does not necessarily need to be performed on the cornea, but can be performed on a separate lens or inlay 430. Inlay 430 is preferably a substantially circular polymeric or synthetic inlay or blank that has a predetermined thickness and a first side 432 and a second side 434 and is positioned under the flap adjacent second surface 26 to correct refractive error in the eye. For a more complete description of use of an inlay, see U.S. Pat. No. 6,197,019 to Peyman, the entire contents of which are herein incorporated by reference.

As described above and seen in FIGS. 18 and 19, a reshaping device 420 having a first surface 422 and a second surface 424 is placed over the inlay 430 adjacent first second surface 434 and heated to the appropriate temperature using a laser 36. Since the inlay is a polymer and is not formed from living cells, there is no need to keep the temperature at or about 60° Celsius (140° F.). The rise in temperature of the lens causes the inlay 430 to soften or become a gelatinous material and thereby flowable which allows the inlay to conform to the shape of the inner surface 422 of reshaping device 420. In a similar manner to that described for the cornea above.

Figure 20:
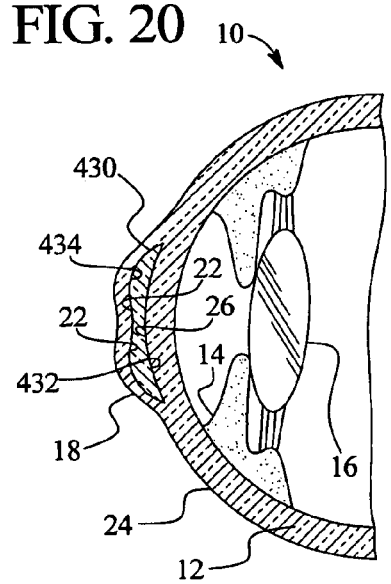
FIG. 20 is a side elevational view in cross section of the eye of FIG. 19 with the lens removed and the flap repositioned over the reformed inlay.

As seen in FIG. 20, once the reshaping device 420 is removed, the flap 18 is placed over the inlay 430. First internal surface 22 is positioned so that it overlies the second surface 434 of inlay 430 without substantial tension thereon. In other words, the flap is merely laid overtop of the inlay 430 so as to not cause undue stress or tension in the flap and possibly causing damage thereto.

It is noted that the method of FIGS. 17–20 is not limited to the first herein described method using a reshaping device and a laser, but can be used with any heating means, such as the container method and the thermally conductive plate method also described herein and any other method that would heat a reshaping device overlying the inlay to the appropriate temperature.

Additionally, this method of FIGS. 17–20 can be preformed with a lens that has a predetermined refractive index, is a blank having no refractive index or a lens that has been modified by a laser, a cryolathe or any other method known in the art to have a predetermined refractive index. For example, with a blank, the inlay can have no refractive power, the entire corrective change in the lens coming from the conformation to the inner surface of reshaping device 420 or the inlay can have refractive power with the reshaping device 420 simply modifying the refractive properties.

Although, the method shown in FIGS. 17–20 uses a lens to correct myopic error, this method can be used to change the shape of the cornea in any manner desired, such to correct astigmatic or hyperopic error in the cornea.

Furthermore, since this method is substantially similar to the methods described above, the description of those methods along with the reference numerals used therein apply to this method.

While various advantageous embodiments have been chosen to illustrate the invention, it will be understood by those skilled in the art that various changes and modifications can be made therein without departing from the scope of the invention as defined in the appended claims.

What is claimed is:

1. A method of correcting the refractive error in the cornea of an eye, comprising the steps of
    positioning a reshaping device having a predetermined first surface adjacent an exposed internal corneal surface, so that the reshaping device overlies a portion of the exposed internal corneal surface,
    heating the reshaping device using a liquid with a predetermined temperature, which in turn heats the cornea to soften the portion of the exposed internal corneal surface that the reshaping device overlies,
    administering the liquid through an irrigation port in the reshaping device, and
    reshaping the softened portion of the exposed internal corneal surface, so that the exposed internal corneal surface substantially conforms to the predetermined first surface of the reshaping device.

2. A method according to claim 1, further comprising the steps of
    monitoring the temperature of the reshaping device using at least one thermocouple; and
    maintaining the temperature of the reshaping device at a substantially uniform temperature.

3. A method according to claim 1, wherein the positioning step is preceded by the steps of:
    separating a portion of the cornea to form a flap; and
    moving the flap to expose an internal corneal surface;
    and the positioning step includes positioning the reshaping device adjacent the internal corneal surface;
    and further comprising the step of
    repositioning the flap, so that it overlies the exposed internal corneal surface.

4. A method according to claim 1, wherein the positioning step is preceded by the steps of:
    separating a portion of the cornea to form a flap; and
    moving the flap to expose an internal corneal surface;
    and further comprising the steps of
    removing the reshaping device, and
    repositioning the flap, so that it overlies the exposed internal corneal surface.

5. A method according to claim 1, wherein
    the positioning step includes positioning a reshaping device configured to correct myopia.

6. A method according to claim 1, wherein
    the positioning step includes positioning an reshaping device configured to correct hyperopia.

7. A method according to claim 1, further comprising the step of
    removing the liquid through an aspiration port in the reshaping device.

8. A method of correcting the refractive error in the cornea of an eye, comprising the steps of
- separating a portion of the cornea to form first and second internal surfaces,
- moving the first surface away from the second surface,
- positioning a reshaping device having a predetermined first surface adjacent the second internal surface, so that the reshaping device overlies a portion of the cornea,
- heating the reshaping device using a liquid with a predetermined temperature, which in turn heats the cornea to soften the portion of the cornea that the reshaping device overlies,
- administering the liquid through an irrigation port in the reshaping device, and
- reshaping the softened portion of the cornea, so that the cornea substantially conforms to the predetermined first surface of the reshaping device.

9. A method according to claim 8, further comprising the steps of
- monitoring the temperature of the reshaping device using at least one thermocouple; and
- maintaining the temperature of the reshaping device at a substantially uniform temperature.

10. A method according to claim 8, wherein
- the heating step includes heating the reshaping device so that the heat is distributed substantially uniformly through the reshaping device.

11. A method according to claim 8, further comprising the steps of
- removing the reshaping device, and
- repositioning the first surface, so that it overlies the second surface.

12. A method according to claim 8, wherein
- the positioning step includes positioning a reshaping device configured to correct myopia.

13. A method according to claim 8, wherein
- the positioning step includes positioning an reshaping device configured to correct hyperopia.

14. A method according to claim 8, further comprising the step of
- removing the liquid through an aspiration port in the reshaping device.

* * * * *